(12) United States Patent
Kuzma et al.

(10) Patent No.: US 7,805,202 B2
(45) Date of Patent: Sep. 28, 2010

(54) IMPLANTABLE ELECTRODES AND INSERTION METHODS AND TOOLS

(75) Inventors: Janusz A. Kuzma, Parker, CO (US); Todd Kevin Whitehurst, Santa Clarita, CA (US); Lani A. Smith, Parker, CO (US); Chuladatta Thenuwara, Castaic, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 473 days.

(21) Appl. No.: 11/241,158

(22) Filed: Sep. 30, 2005

(65) Prior Publication Data

US 2007/0078503 A1 Apr. 5, 2007

(51) Int. Cl.
*A61N 1/02* (2006.01)

(52) U.S. Cl. ....................................... 607/116

(58) Field of Classification Search ................. 606/129, 606/130; 607/46, 115–119; 600/382–391
See application file for complete search history.

(56) References Cited

U.S. PATENT DOCUMENTS

| | | | | |
|---|---|---|---|---|
| 4,580,561 A | * | 4/1986 | Williamson | 606/130 |
| 5,193,539 A | | 3/1993 | Schulman et al. | |
| 5,193,540 A | * | 3/1993 | Schulman et al. | 607/61 |
| 5,269,304 A | * | 12/1993 | Matthews | 607/46 |
| 5,312,439 A | | 5/1994 | Loeb | |
| 6,051,017 A | | 4/2000 | Loeb et al. | |
| 6,501,981 B1 | * | 12/2002 | Schweikard et al. | 600/427 |
| 6,609,032 B1 | | 8/2003 | Woods et al. | |
| 6,662,036 B2 | * | 12/2003 | Cosman | 600/411 |
| 6,829,508 B2 | * | 12/2004 | Schulman et al. | 607/116 |

(Continued)

FOREIGN PATENT DOCUMENTS

WO  WO 98/37926  9/1998

(Continued)

OTHER PUBLICATIONS

U.S. Appl. No. 11/040,209, filed Jan. 20, 2005 by Colvin et al., entitled "Implantable Microstimulator with Plastic Housing and Methods of Manufacture and Use" (not published).
U.S. Appl. No. 11/056,762, filed Feb. 11, 2005 by He, T. X., entitled "An Implantable Microstimulator Having a Separate Battery Unit and Methods of Use Thereof" (not published).

*Primary Examiner*—Scott M Getzow
*Assistant Examiner*—Amanda Patton
(74) *Attorney, Agent, or Firm*—Frommer Lawrence & Haug LLP; Bruce E. Black

(57) ABSTRACT

An insertion kit for implanting an electrode in a patient can include a handle; an insertion member coupled to the handle at a proximal end of the insertion member and configured and arranged to be inserted into a patient; an alignment member coupled to the handle and disposed over the distal end of the insertion member; and an electrode configured and arranged to be inserted into the patient using the insertion member. In some instances, the insertion kit may also include one or more of a marker that cooperates with the alignment member to mark a position of the electrode on the skin of the patient; a pointer that cooperates with the alignment member to find the marked position on the skin of the patient; and a second electrode and a second insertion member configured and arranged for detachably coupling to the handle in place of the insertion member.

20 Claims, 19 Drawing Sheets

U.S. PATENT DOCUMENTS

| | | | |
|---|---|---|---|
| 6,872,213 B2 * | 3/2005 | Chakeres | 606/130 |
| 7,063,708 B2 * | 6/2006 | Gibson et al. | 606/129 |
| 7,288,096 B2 * | 10/2007 | Chin | 606/129 |
| 2004/0059392 A1 | 3/2004 | Parramon et al. | |

FOREIGN PATENT DOCUMENTS

| | | |
|---|---|---|
| WO | WO 98/43700 | 10/1998 |
| WO | WO 98/43701 | 10/1998 |

* cited by examiner

IMPLANTABLE ELECTRODES AND INSERTION METHODS AND TOOLS

FIELD

The invention is directed to implantable electrodes and microstimulators and methods and tools for insertion of the electrodes into a patient's body. In addition, the invention is directed to implantable electrodes and microstimulators for stimulating the occipital nerve.

BACKGROUND

Implantable microstimulators have been developed to provide therapy for a variety of disorders, as well as other treatments. For example, implantable microstimulators can be used in neurological therapy by stimulating nerves or muscles, for treating headaches and migraines by stimulating the occipital nerve, for urinary urge incontinence by stimulating nerve fibers proximal to the pudendal nerves of the pelvic floor, for erectile and other sexual dysfunctions by stimulating the cavernous nerve(s), for reduction of pressure sores or venous stasis, etc.

Implantable microstimulators, such as the BION® device (available from Advanced Bionics Corporation, Sylmar, Calif.), can be used to provide electrical stimulation. Even though these devices can be quite small, there are some instances in which placement of the device next to the tissue to be stimulated may be undesirable. In these instances, one or more electrodes can be positioned near the tissue to be stimulated and the microstimulator can be implanted elsewhere and coupled to the electrode(s) by a lead. The electrodes should be placed in a position that is effective for stimulation of the selected tissue. Correctly positioning such small devices can often be difficult or time consuming.

BRIEF SUMMARY

One embodiment is an insertion kit for implanting an electrode in a patient. The insertion kit includes a handle; an insertion member coupled to the handle at a proximal end of the insertion member and configured and arranged to be inserted into a patient; an alignment member coupled to the handle and disposed over the distal end of the insertion member; and an electrode configured and arranged to be inserted into the patient using the insertion member. In some instances, the insertion kit may also include one or more of a marker that cooperates with the alignment member to mark a position of the electrode on the skin of the patient; a pointer that cooperates with the alignment member to find the marked position on the skin of the patient; and a second electrode and a second insertion member configured and arranged for detachably coupling to the handle in place of the insertion member.

Another embodiment is a method of stimulating tissue in a patient. The method includes providing an insertion tool; making an incision in the body of the patient; and inserting a portion of the insertion tool through the incision. An electrode is inserted into the body using the insertion tool. A placement position for the electrode proximate to the tissue to be stimulated is determined. The electrode is detached from the insertion tool at the placement position. The insertion tool is withdrawn from the body of the patient leaving the electrode in the placement position.

Yet another embodiment is a stimulating electrode that includes a conductive electrode body having a front surface and a back surface; a raised rim disposed around an edge of the electrode body; and protrusions extending from the back surface for engagement with surrounding tissue to assist in retaining the stimulating electrode at a placement position in a body of a patient.

Another embodiment is an insertion kit for implanting an electrode in a patient. The kit includes a first inserter; a first electrode disposed in the first inserter; a second electrode; a second inserter; a handle; and an insertion member coupled to the handle at a proximal end of the insertion member and configured and arranged to be inserted into a patient. The insertion member defines a hollow tube through which the first electrode can be inserted into the patient using the first inserter and a second electrode can be inserted into the patient using the second inserter.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1:
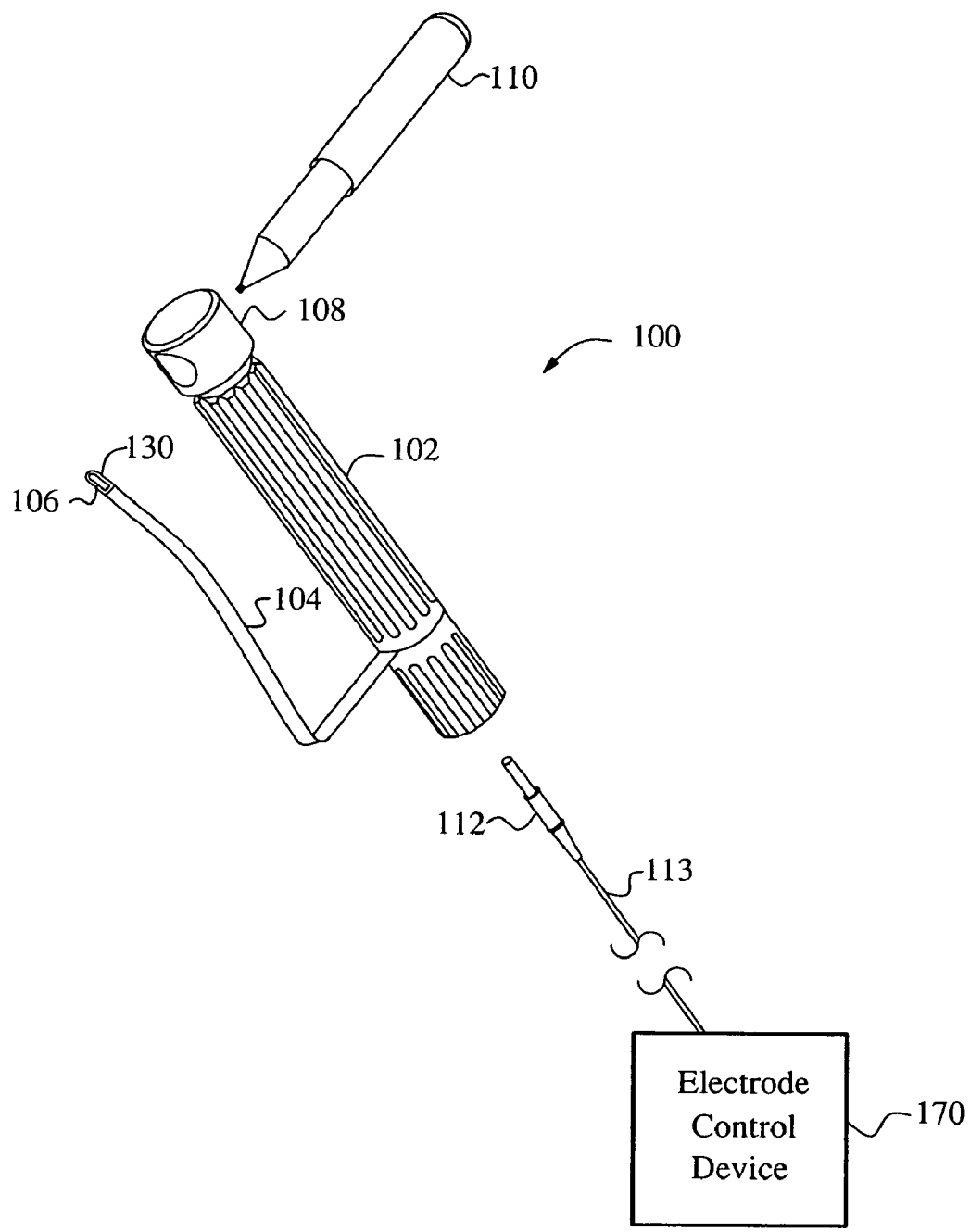
FIG. 1 is a schematic side view of one embodiment of an insertion tool, according to the invention.

The present invention is directed to implantable electrodes and microstimulators and methods and tools for insertion of the electrodes into a patient's body. In addition, the present invention is directed to implantable electrodes and microstimulators for stimulating the occipital nerve and also includes implantation methods and tools.

The implantable microstimulators can be used to stimulate nerves and other tissues. For example, the implantable microstimulators can be used to stimulate the occipital nerve. One or more (for example, two) microstimulators can be implanted near one or more branches of the occipital nerve. These implantable microstimulators can be used to treat disorders such as, for example, headaches or migraines. The use and implantation of the microstimulators will be exemplified below relative to implantation of electrodes near the occipital nerve. It will be recognized, however, that these electrodes and their corresponding microstimulators can also be implanted near other nerves or tissues using similar methods, tools, and microstimulator or electrode configurations.

Examples of suitable implantable microstimulators that can be used or modified for use in stimulating a nerve include, but are not limited to, microstimulators described in U.S. Pat. Nos. 5,193,539; 5,193,540; 5,312,439; 6,051,017; and 6,609,032; U.S. Patent Application Publication No. 2004/059392; U.S. patent applications Ser. Nos. 11/040,209 and 11/056,762; and PCT Patent Applications Publication Nos. 98/37926; 98/43700; and 98/43701, all of which are incorporated herein by reference.

A microstimulator arrangement can include at least one microstimulator unit and one or more electrodes attached by one or more leads to the microstimulator unit(s). The electrodes can be implanted near the occipital nerve (or other nerve or tissue) using an insertion tool that facilitates finding the proper position for the electrode to provide the desired stimulation. The insertion tool includes a handle and an insertion member. The insertion member is inserted into the patient's body through an incision and includes an electrode typically disposed at a distal end of the insertion member. The proximal end of the insertion member is attached to the handle. The handle is used to guide the electrode disposed in the insertion member to a suitable position for stimulation of the desired tissue. Stimulation signals can be sent to the electrode during the positioning procedure and the results observed to assist in finding the desired placement position for the electrode.

In one embodiment, the electrode used to identify a suitable position for stimulation is a test electrode. The position identified during this process can be marked on the skin of the patient using a marker that cooperates with an alignment member coupled to the handle. The test electrode and insertion member can then be removed through the incision. A second insertion tool (or the same insertion tool that has been reconfigured) including a microstimulator electrode can then be inserted through the incision. The position marked on the skin of the patient can be found and aligned using the alignment member. The microstimulator electrode can then be detached from the electrode holder of the insertion member and left in the patient. The insertion tool is removed from the patient. The microstimulator electrode can be connected to a microstimulator unit using a lead attached to the microstimulator electrode. The microstimulator unit can then be implanted in a convenient place, for example, at the base of the skull under the trapezius muscles and the incision can be closed.

In another embodiment, the insertion member can remain in place and the test electrode can be removed from the insertion member. The microstimulator electrode can then be inserted through the insertion member to the desired position without substantially moving the insertion tool. The microstimulator electrode can then be detached and the insertion tool removed from the patient.

FIG. 1 illustrates one embodiment of an insertion tool 100 which includes a handle 102, an insertion member 104 with an electrode holder 130, an electrode 106, an alignment member 108, and a marker 110. The insertion tool 100 can also include a receptacle (not shown) to receive a connector 112 that is coupled by a cord 113 to an electrode control device 170. The electrode control device can be used to provide signals to the electrode 106 during or after the positioning process. The insertion tool 100 can be used, for example, to identify the position for placement of a microstimulator electrode by providing stimulation signals from the electrode control device to the electrode. The results of the stimulation signals can be monitored to identify a desirable placement site for the microstimulator electrode. The electrode 106 in this embodiment can be a mapping electrode to assist in determining a suitable position for the subsequently implanted microstimulator electrode.

Figure 2:
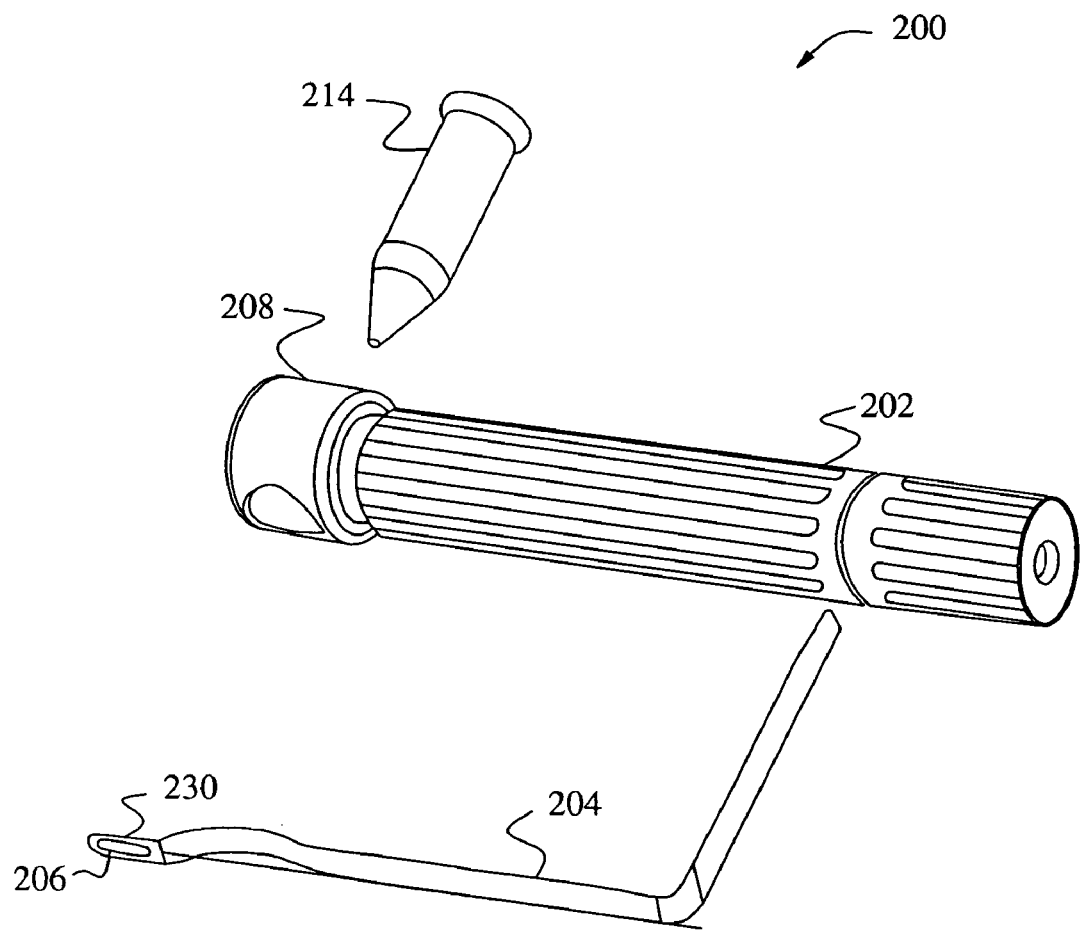
FIG. 2 is a schematic side view of one embodiment of another insertion tool, according to the invention.

FIG. 2 illustrates another embodiment of an insertion tool 200 which includes a handle 202, an insertion member 204 with an electrode holder 230, an electrode 206, an alignment member 208, and a pointer 214. The insertion tool 200 can be used, for example, to implant a microstimulator electrode (e.g., electrode 206) within the patient. The alignment member 208 and the pointer 214 can be used to align the insertion tool 200 with the mark made using the insertion tool 100 and the marker 110. The microstimulator electrode 206 can then be released from the insertion tool 200 and left in the patient.

Insertion tools 100, 200 can be used cooperatively in identifying a position for and in placing a microstimulator electrode. In some embodiments, insertion tools 100, 200 may include some components that are used for both tools such as, for example, the handle 102, 202, the alignment member 108, 208, and even, in some instances, the insertion member 104, 204. In some embodiments, the insertion tool 100 can be reconfigured to form the insertion tool 200. For example, the insertion tool 100 can be used to identify the proper position and then portions of the tool (e.g., the electrode 106, the marker 110, and, optionally, the insertion member 104) can be replaced by different components (e.g., the electrode 206, the pointer 214, and, optionally, the insertion member 204) to form the insertion tool 200.

The handle 102, 202 can be formed of any material and, preferably, has a texture that facilitates gripping of the handle and maneuvering of the electrode 106, 206 within the body of the patient. The handle 102, 202 also preferably includes a mechanism for attachment or coupling of the insertion member 104, 204 to the handle. In some embodiments, the attachment between handle and insertion member is permanent. In other embodiments, the insertion member is removably attached to the handle. Preferably, any attachment mechanism is sufficiently robust to maintain attachment of the insertion member to the handle during expected usage conditions.

In at least some embodiments, attaching the insertion member to the handle also results in the formation of a path to allow electrical communication between the electrode 106 and the receptacle which receives the connector 112 from the electrode control device. This allows stimulation signals to be provided between the electrode control device 170 (FIG. 1) and the electrode 106.

The alignment member 108, 208 is removably or integrally attached to the handle 102, 202 and, preferably, is disposed over the distal end of the insertion member 104, 204 at which the electrode 106, 206 is positioned. The alignment member 108, 208 assists in aligning the second insertion tool 200 with the position identified by the first insertion tool 100 for placement of the microstimulator electrode. For example, the alignment member 108, 208 can define an opening through which a marker 110 can be disposed to mark the position identified using electrode 106 or through which a pointer 214 can be disposed to align the second insertion tool 200 with the marked position.

The marker 110 can be any marking device, e.g., a marker, pen, or pencil, that can be used to make a mark on the patient's skin. Preferably, the marker 110 fits snugly in the alignment member 108 to more exactly mark the desired electrode position and to facilitate the correct alignment of the second insertion tool 200 with the position identified using the electrode 106.

The pointer 214 can be any device that can be used to align the insertion tool 200 with the mark made by the marker 110. For example, the pointer 214 can be configured so that the practitioner looks down a hollow barrel of the pointer to identify when the mark has been reached or the pointer can be configured so that the practitioner merely observes the tip of the pointer from an angle to verify alignment of the pointer tip with the mark on the skin of the patient.

The insertion members are constructed to be sufficiently robust for performing the insertion, positioning, and withdrawal procedures. In some embodiments, the insertion members have a construction that provides a right angle between a distal portion that holds the electrode and a proximal portion that attaches to the handle. Any of the insertion members described herein can be straight or curved. For example, the portion of the insertion member inserted into the patient may be curved to roughly follow the curvature of the scalp of the patient.

Figure 3:
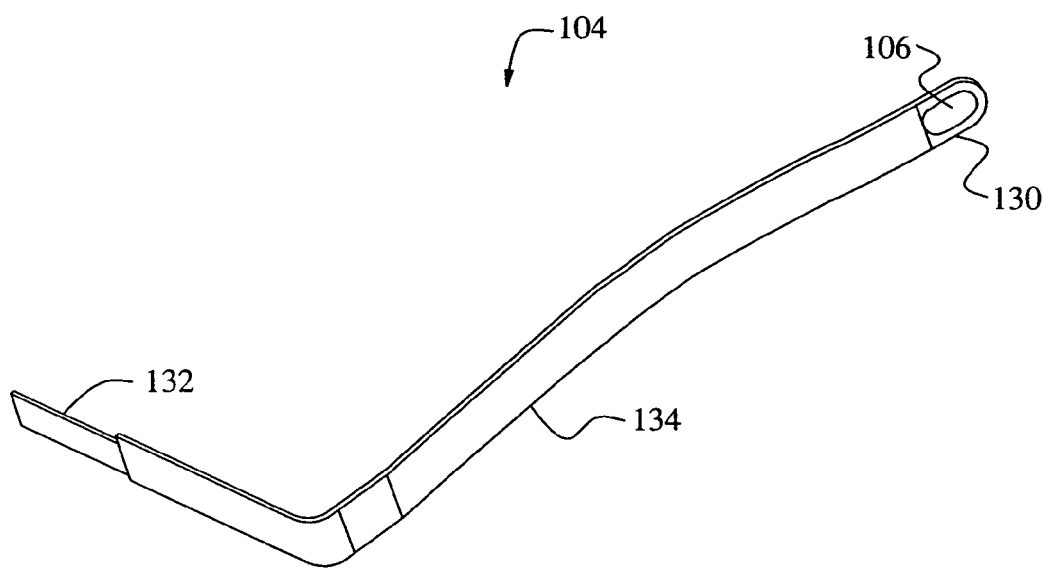
FIG. 3 is a schematic perspective view of one embodiment of an insertion member of the insertion tool of FIG. 1.

One embodiment of an insertion member 104 is illustrated in FIG. 3 and includes an electrode holder 130 to hold the electrode 106, a conductive connector 132, and an electrically insulating covering 134. In this embodiment, the electrode holder is formed around the electrode 106 to hold the electrode firmly in place during insertion of the insertion member, positioning of the electrode to determine a placement for the microstimulator electrode, and withdrawal of the insertion member. The leading edge of the electrode holder 130 also pushes aside or dissects the tissue as the insertion member 104 is guided through the patient's body.

The conductive connector 132 is configured to be coupled to the handle 102 to hold the insertion member 104 firmly and to also provide electrical communication between the electrode 106 and the electrode control device 170 (FIG. 1) via the connector 112 and the cord 113. For example, the conductive connector can be a strip of metal that runs along the length of the insertion member 104 and makes contact with the electrode 106. The electrically insulating covering 134 is preferably provided over at least that portion of the insertion member 104 which is inserted into the patient, with the possible exception of the region of the connector 132 near the electrode 106. This protects the patient from electrical current running through the insertion member 104 to the electrode 106 and also facilitates focusing the stimulating current at the desired location near the electrode.

The electrode 106 can be formed entirely of a single conductive material, such as a metal or alloy, or the electrode can be formed using a combination of conductive materials such as, for example, a conductive coating over a bulk metallic electrode. In other embodiments, the electrode 106 can be formed from a polymeric material that is at least partially, or fully, coated with a conductive coating, such as a metal, alloy, or conductive oxide (e.g., iridium oxide) coating.

Typically, the electrode 106 is sufficiently robust to withstand the insertion and positioning process. Preferably, the electrode 106 is held firmly in place in the electrode holder 130 during insertion and withdrawal of the insertion member 104 from the patient's body.

Figure 4:
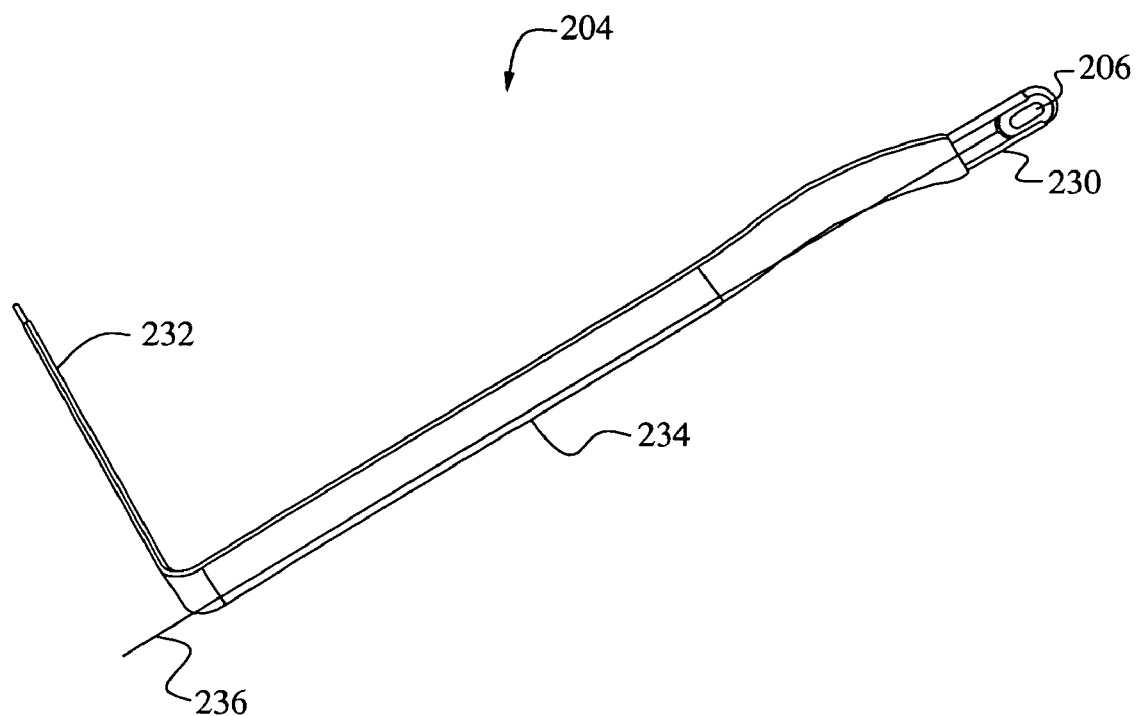
FIG. 4 is a schematic perspective view of one embodiment of an insertion member of the insertion tool of FIG. 2.

Turning to FIG. 4, one embodiment of the insertion member 204 includes an electrode holder 230, a connector 232, and an insertion arm 234. An electrode 206 is disposed in the electrode holder 230 with a lead 236 attached to the electrode 206 and, preferably, trailing along the insertion arm 234. The lead can be attached to a microstimulator unit during or subsequent to implantation of the electrode 206. The connector 232 is configured to be attached to the handle 102 to hold the insertion member 204 firmly during insertion, positioning, detachment of the electrode 206 from the electrode holder 230 (as described below), and withdrawal. In this embodiment, the connector 232 does not typically carry electrical signals to the electrode 206 and so the connector 232 and insertion arm 234 can be made of insulating material, if desired. Conductive materials can also be used if the connector 232 and insertion arm 234 are electrically insulated from the electrode 206 or if the electrode is not energized until after detachment from the electrode holder 230. In addition, the connector 232 and insertion arm 134 can be integrally formed, if desired.

Figure 5:
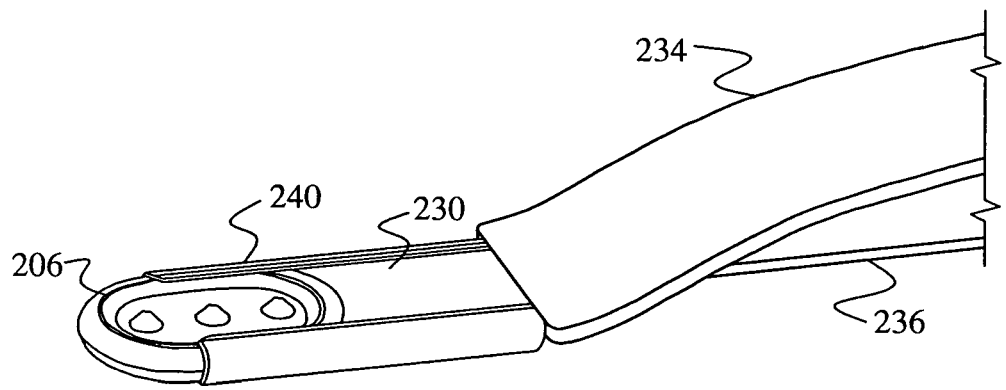
FIG. 5 is schematic perspective view of one embodiment of an electrode holder for the insertion member of FIG. 4.
Figure 6:
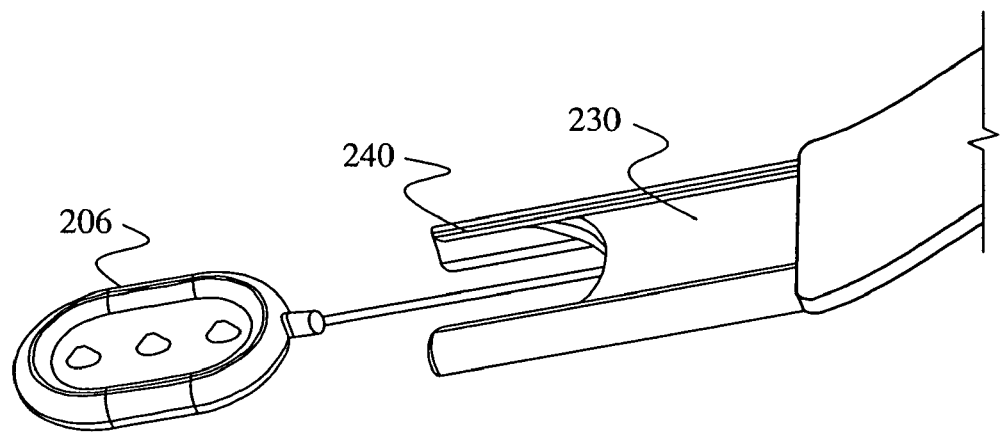
FIG. 6 is a schematic perspective view of the release of a microstimulator electrode from the electrode holder of FIG. 5.
Figure 7:
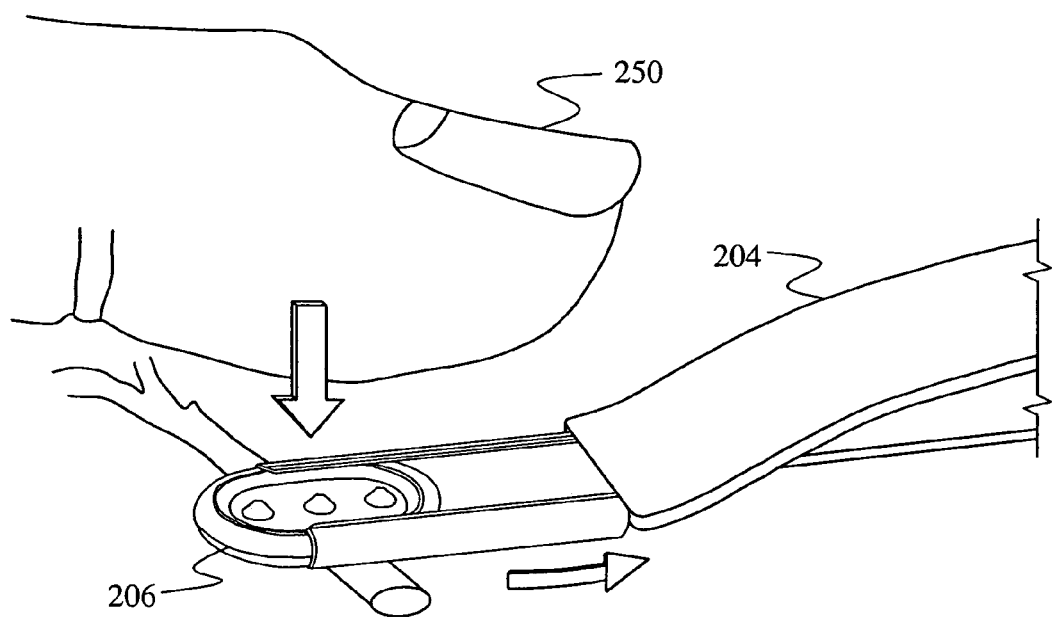
FIG. 7 is a schematic perspective view of a method for the release of a microstimulator electrode from the electrode holder of FIG. 5.

The electrode holder 230 is designed to hold the electrode 206 during insertion of the insertion member 204 into the patient and placement of the electrode in the desired position. The electrode holder 230 is also designed to allow disengagement of the electrode 206 and withdrawal of the insertion member 204 so that the electrode remains implanted within the patient. FIG. 5 illustrates one embodiment of the electrode holder 230. This embodiment includes at least one pair of opposing rails 240 (and, preferably, at least two opposing pairs of rails) into which the electrode 206 can be introduced prior to insertion of the insertion member 204 into the patient. Preferably, the rails provide sufficient frictional engagement with the electrode 206 to retain the electrode within the electrode holder during insertion into the patient and positioning of the electrode in the desired placement site even if the movement of the insertion member results in partial withdrawal of the insertion member from the patient. The rails, preferably, slidingly engage the electrode 206 and allow detachment of the electrode when force is applied to the electrode to hold it in place during withdrawal of the insertion member 204, as illustrated in FIG. 6. For example, as illustrated in FIG. 7, the practitioner can apply pressure using a finger or thumb 250 against the skin of the patient over the electrode 206 to hold the electrode in place during detachment of the electrode and withdrawal of the insertion member 204.

The electrode 206 can be formed entirely of a single conductive material, such as a metal or alloy, or the electrode can be formed using a combination of conductive materials such as, for example, a conductive coating over a bulk metallic electrode. In other embodiments, the electrode 206 can be formed from a polymeric material that is at least partially, or fully, coated with a conductive coating, such as a metal, alloy, or conductive oxide (e.g., iridium oxide) coating.

Figure 8A:
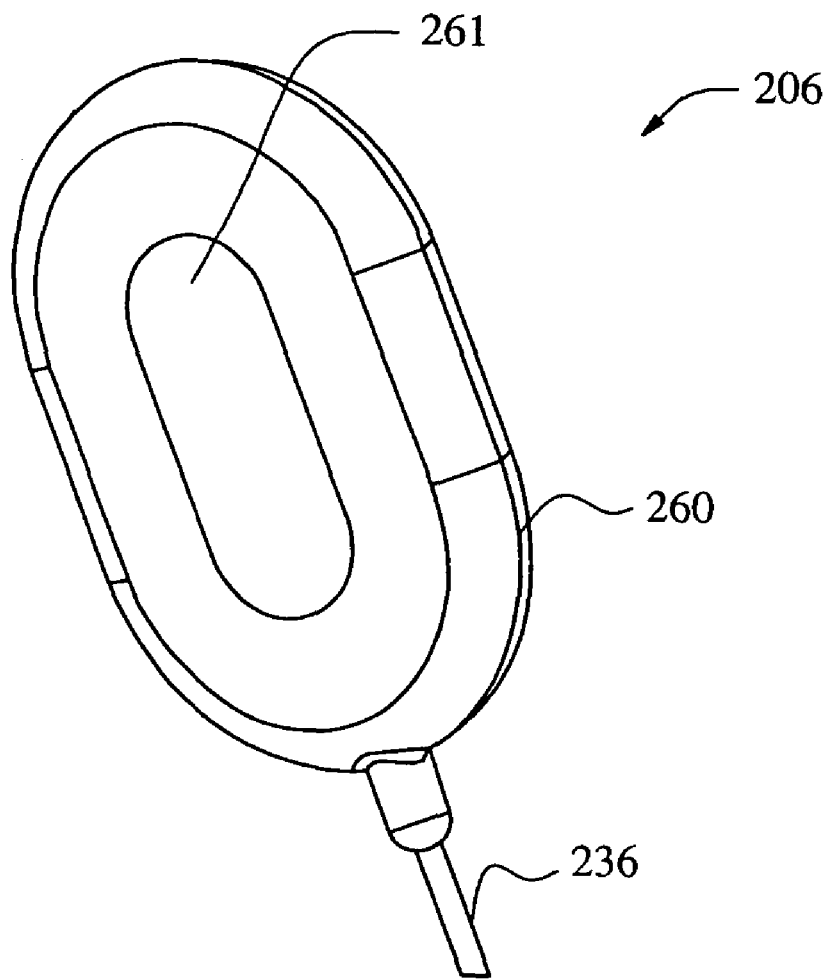
FIGS. 8A and 8B are schematic perspective front and back views, respectively, of a microstimulator electrode, according to the invention.
Figure 8B:
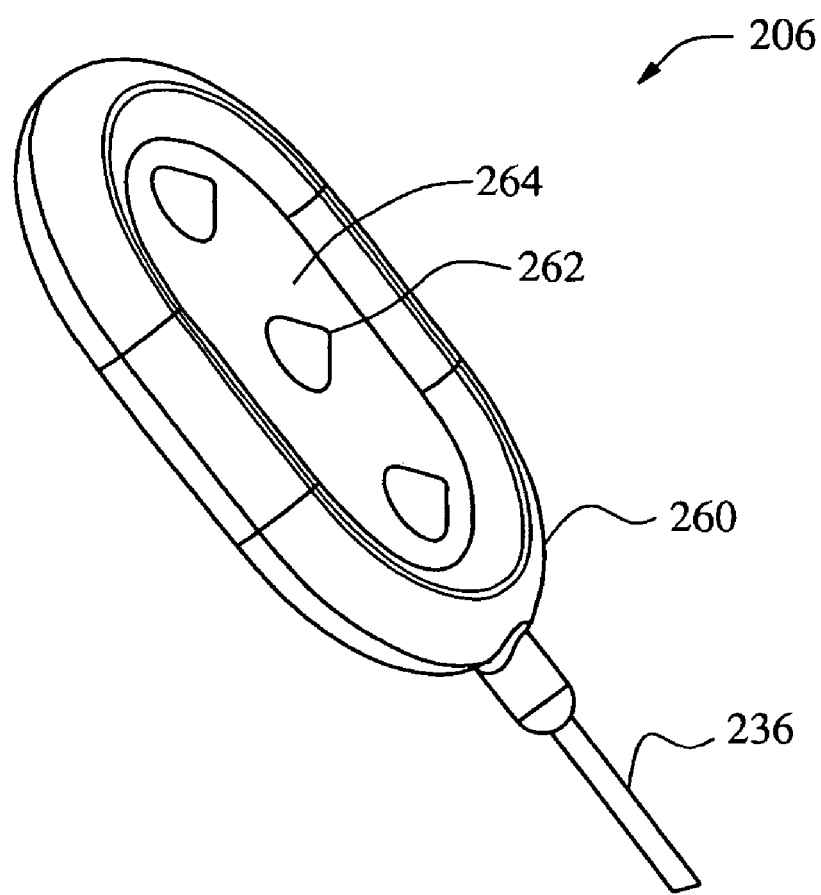

One embodiment of a suitable electrode 206 is illustrated in FIGS. 8A and 8B. The electrode 206 can have a raised rim 260 for engagement with the rails 240 of the electrode holder 230. This rim can be made of a conductive material or can be made of a non-conductive material such as a plastic or rubber material. The electrode has a front surface 262, which preferably faces the tissue to be stimulated, and an opposing back surface 264. The electrode optionally has one or more projections 262 disposed on either the front or back surfaces or both (preferably, at least the back surface) which can facilitate detachment of the electrode 206 from the electrode holder 230 when desired. These projections can engage the tissue of the patient, particularly when pressure is applied to the tissue, and resist movement of the electrode away from the placement position during detachment of the electrode 206 from the insertion member 204. These projections can be made of any material including conductive materials such as those forming the electrode itself, or non-conductive materials such as plastic or rubber materials.

Figure 9:
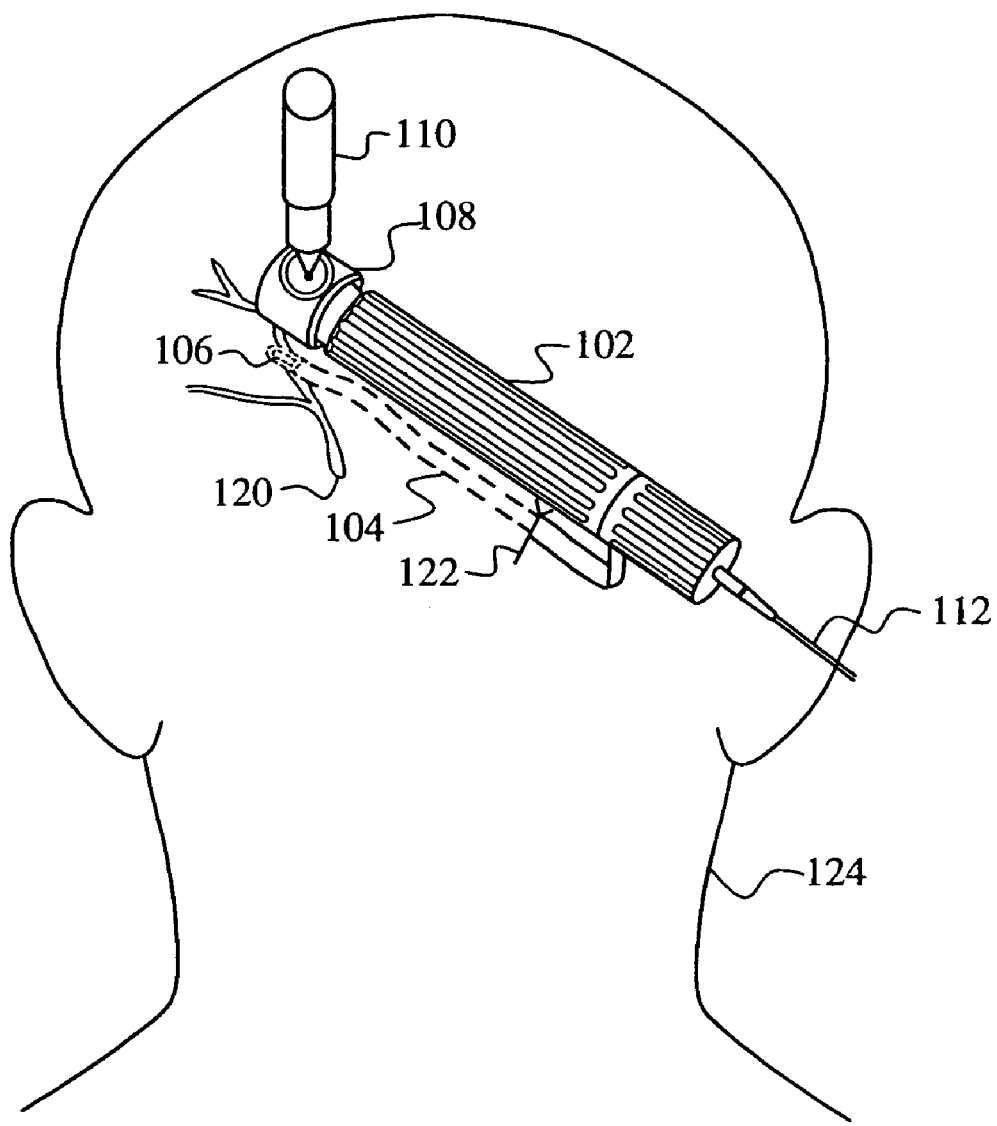
FIG. 9 is a schematic perspective view of a method of utilizing the insertion tool of FIG. 1, according to the invention.

FIG. 9 illustrates the insertion tool 100 in use. An incision 122 is made in the skin of the patient 124 so that the insertion member 104 can be inserted under the skin and into the desired tissue. The practitioner holds the handle 102 and guides the electrode 106 into a suitable placement position with respect to the nerve 120 or other tissue to be stimulated. Preferably, an electrode control device 270 (see FIG. 1) is coupled to the electrode through the connector 112 and stimulation signals are provided to the electrode 106 to assist in positioning the electrode within the patient. For example, the stimulation signals may result in sensations that can be monitored by the patient or practitioner or the practitioner may monitor another device to observe the stimulation effects of the electrode on the surrounding tissue. The marker 110 can be inserted into the alignment member 108 and, when the electrode is in the desired position, the practitioner can use the marker to place an alignment mark on the skin of the patient 124. The insertion member 104 and electrode 106 can then be withdrawn through the incision 122.

Figure 10:
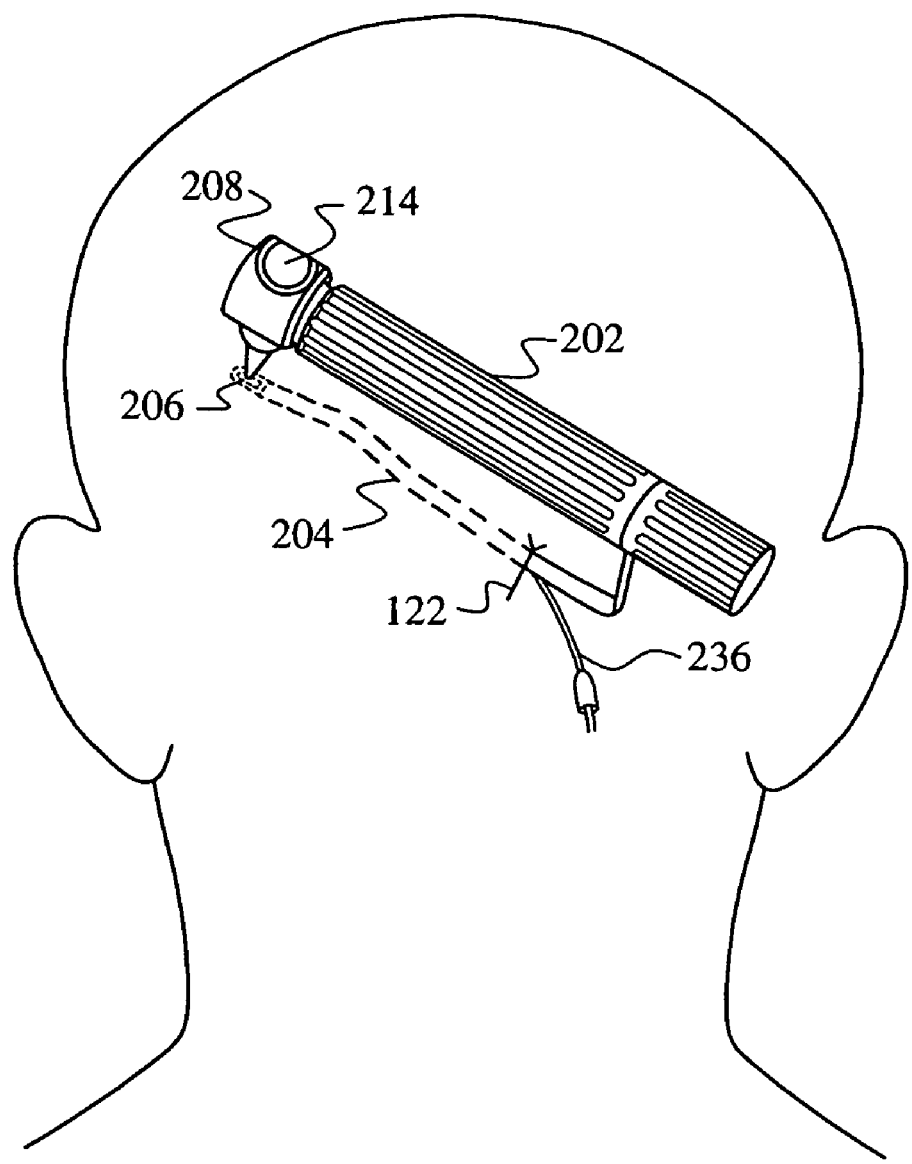
FIG. 10 is a schematic perspective view of a method of utilizing the insertion tool of FIG. 2, according to the invention.

FIG. 10 illustrates the insertion tool 200 in use. The insertion member 204 and electrode 206 are inserted into the patient through the incision 122. The electrode is then guided to the position identified by the insertion tool 100. This position is identified using the alignment member 208 and pointer 214 by observing when the pointer 214 is aligned with the mark made using marker 110. Once the electrode 206 has been properly aligned with the identified placement position, the electrode can be detached from the electrode holder 230 of the insertion member 204 by, for example, applying pressure to the skin over the electrode and withdrawing the insertion member leaving the electrode 206 and lead 236 in place, as illustrated in FIG. 7. The insertion member 204 is then removed from the patient through the incision 122.

In one alternative embodiment, only the insertion tool 200 is used. In this embodiment, the microstimulator electrode is placed in the electrode holder and then inserted into the patient through the incision. The tissue to be stimulated can be determined, if desired, by applying stimulation pulses to the microstimulator electrode using a microstimulator unit (as describe below) or electrode control unit (see FIG. 1) coupled to the microstimulator electrode. The electrode can then be placed by moving the handle until the electrode is in the desired position. The electrode is detached from the electrode holder and the insertion tool is removed. In this embodiment, the first insertion tool (e.g., insertion tool 100) and a separate mapping electrode (e.g., electrode 106) are not used during the implantation process.

There are some advantages to the two insertion tool process described above and illustrated in FIGS. 9 and 10. For example, the electrode 106 can be held firmly in the insertion tool 100 and does not need to detach and, accordingly, there is concern that there will be unwanted detachment of the electrode from the insertion tool during the process of identifying a suitable site for implantation of the microstimulator electrode. In addition, the insertion tool 100 and electrode 106 form a more robust arrangement which facilitates penetrating the tissue to identify the desired site for placement of the microstimulator electrode. Once the tissue has been penetrated, the second tool 200 and microstimulator electrode 206, which have a less robust construction, can follow the path prepared by the first tool. On the other had, a one tool process can be faster and has fewer components to prepare for the surgery.

Figure 15:
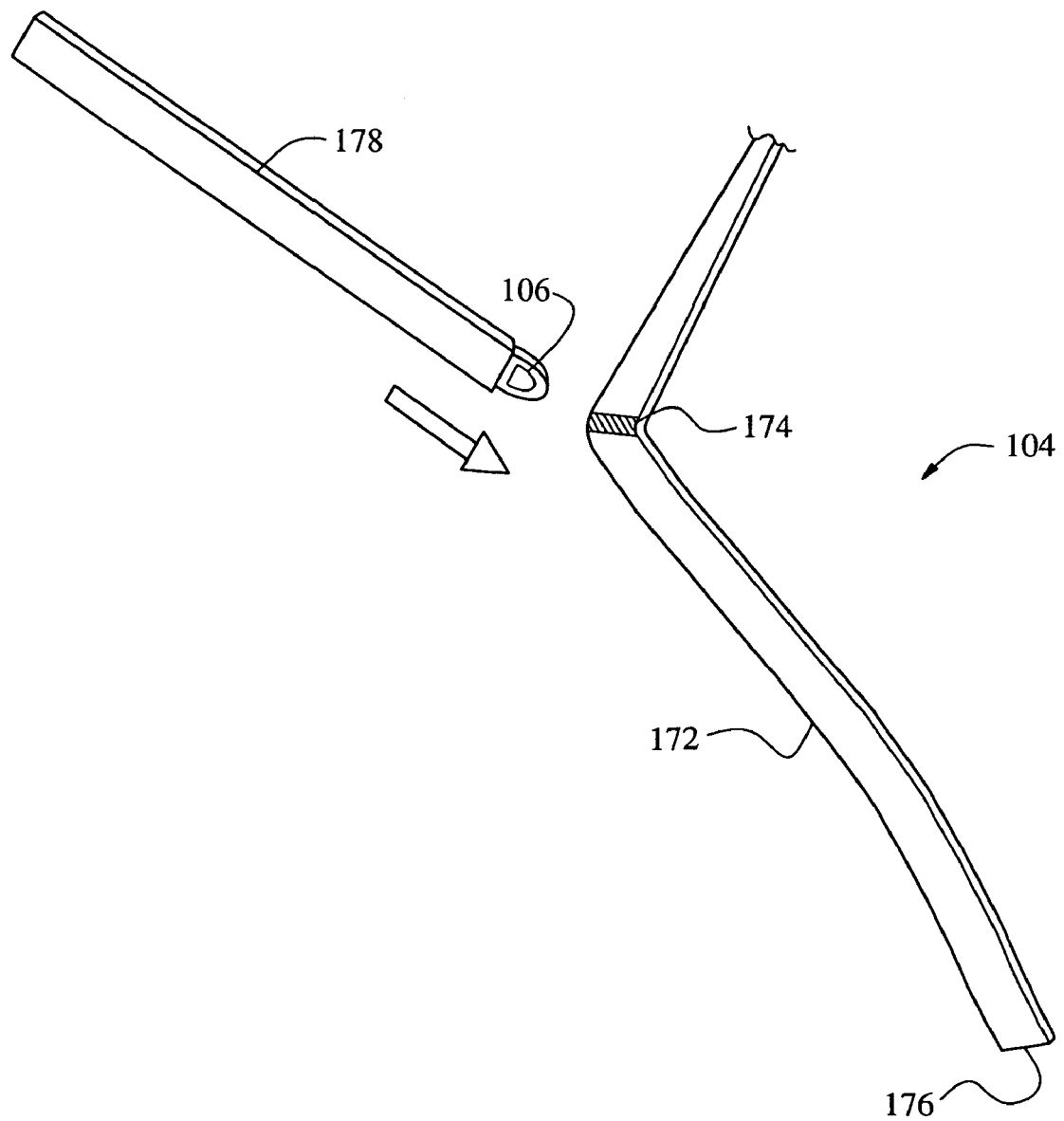
FIG. 15 is a schematic perspective view of another embodiment of an insertion member, according to the invention.
Figure 16:
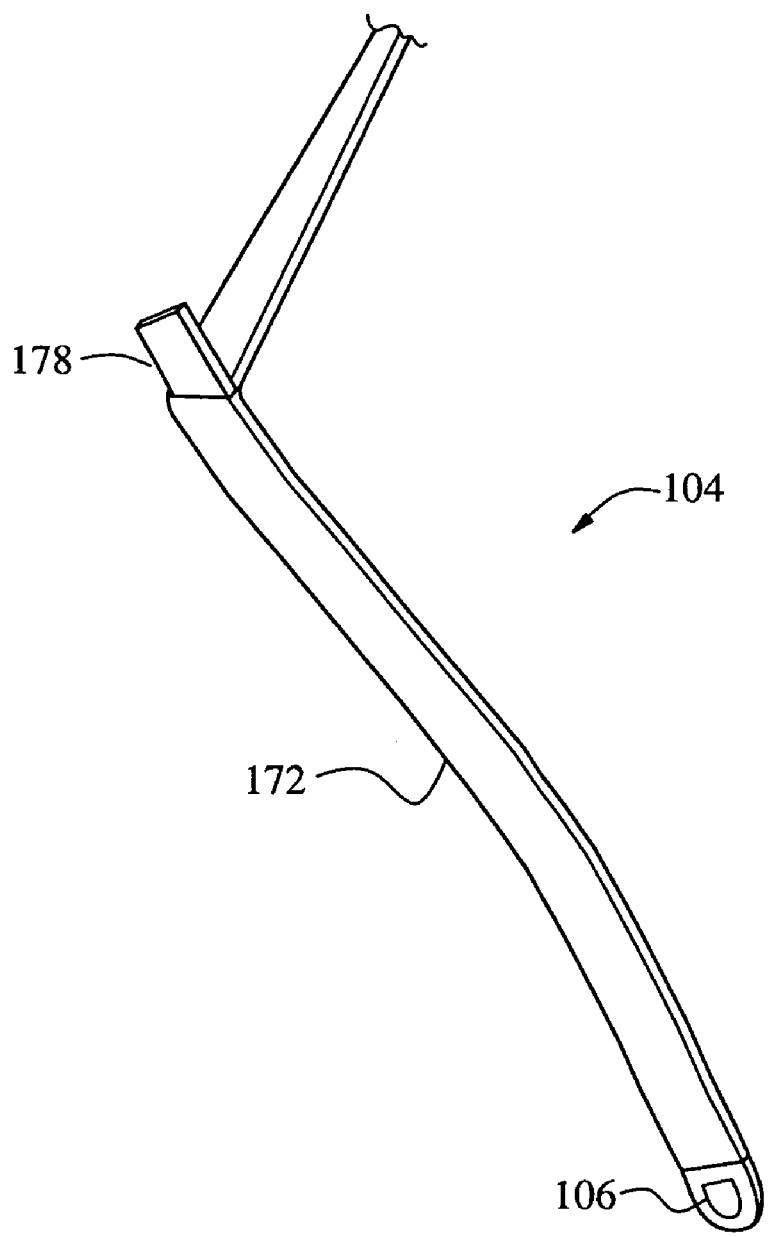
FIG. 16 is a schematic perspective view of the insertion member of FIG. 15 with a first electrode in place.
Figure 17:
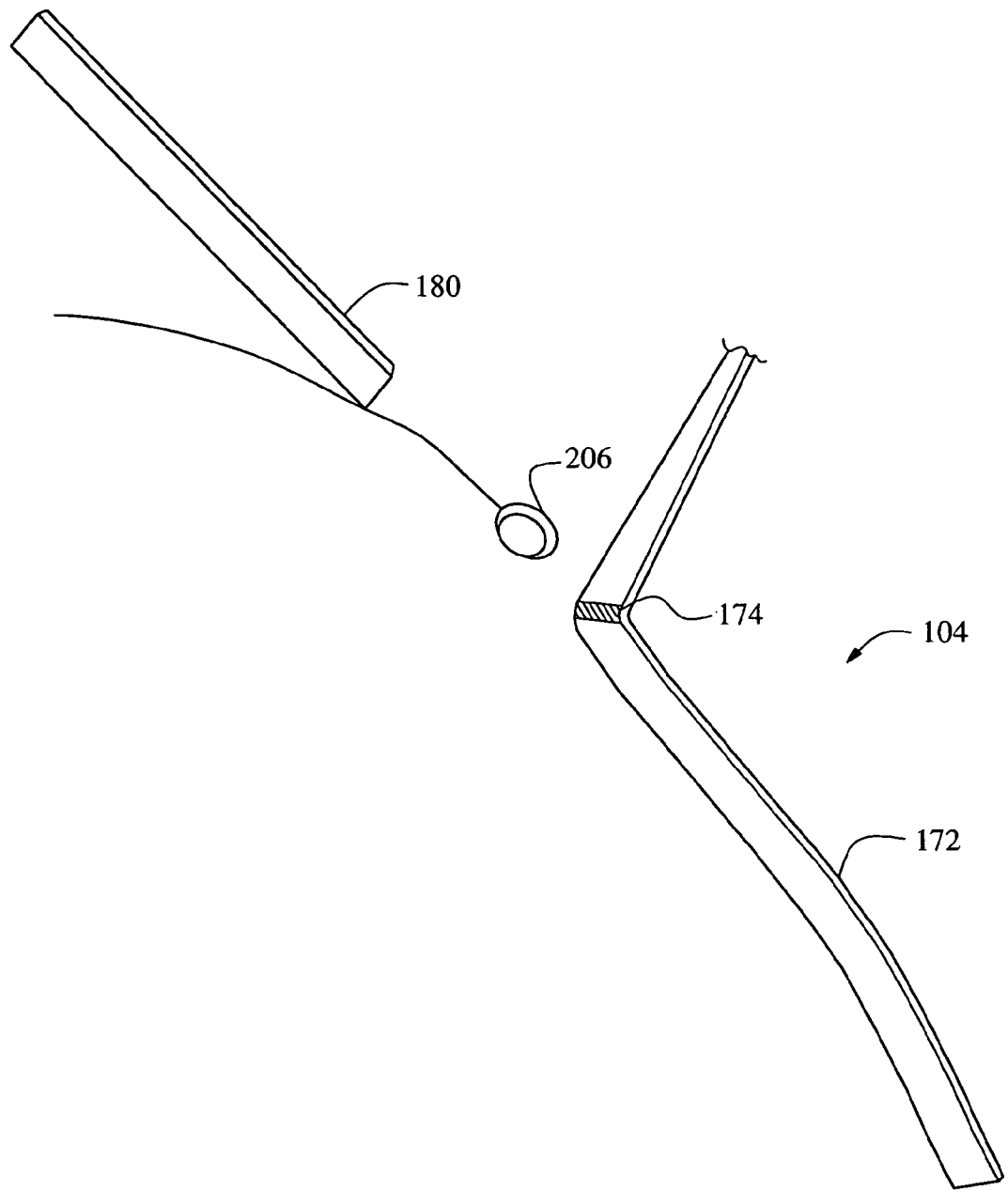
FIG. 17 is a schematic perspective view of the insertion member of FIG. 16 with a second electrode.

FIGS. 15-17 illustrate yet another embodiment of an insertion tool and a method for its use. In this embodiment, the insertion member 104 has a portion 172 that is inserted into the patient and which has the form of a hollow tube with openings 174, 176 at each end. The electrode 106 is carried on an inserter 178 that can be inserted through opening 174 and the electrode 106 can be pushed along the hollow tube of portion 172 until the electrode 106 is pushed out of the opening 176, as illustrated in FIG. 16. The insertion of the electrode 106 and inserter 178 can take place prior to or after inserting the insertion member 104 into the patient. Optionally, there may be a stop at opening 176 or 174 or on inserter 178 to stop inserter 178 when electrode 106 has been pushed through opening 176 or there may be a marking on the inserter to indicate how far the inserter should be pushed through the opening. The electrode 106 is coupled to the electrode control device 170 (FIG. 1) typically through the inserter 178 using a cord or leads or the like.

Once the proper position for stimulation has been determined by moving the insertion tool and using electrode 106 to find the tissue to be stimulated, the electrode 106 and inserter 178 can be removed from the insertion member 104 without removing the insertion member from the patient. A microstimulator electrode 206 can then be inserted into the opening 174 and pushed through the hollow tube of the portion 172 of the insertion member using a second inserter 180 while the insertion member 104 is still in the patient, as illustrated in FIG. 17. This second inserter 180 may be simply a device that pushes on the electrode 206, as illustrated in FIG. 17, or the second inserter may include an electrode holder similar to the electrode holder 230 of FIG. 5. Optionally, there may be a stop at opening 176 or 174 or on inserter 180 to stop inserter 180 when electrode 206 is in the proper place after being pushed through opening 176 or there may be a marking on the inserter to indicate how far the inserter should be pushed through the opening or the practitioner may simply feel when the electrode 206 is in the proper position. After positioning electrode 206, the insertion member 104 can be removed through the incision in the patient leaving the electrode.

In this embodiment, the insertion member 104 may be permanently or removably affixed to the handle (not shown) of the insertion tool. The insertion tool can optionally include an alignment member, marker, and pointer to mark where the position identified with the electrode 106. In some instances, these items may not be used or provided on the insertion tool because the tool does not need to be removed from the patient to insert microstimulator electrode 206.

Figures 18, 19:
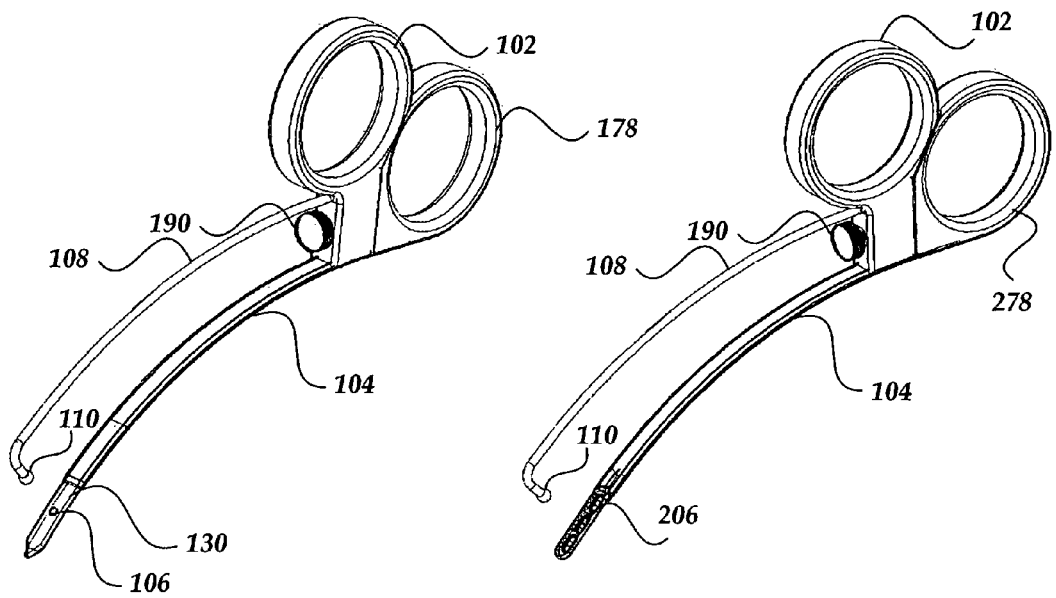
FIG. 18 is a schematic perspective view of another embodiment of an insertion tool with a first electrode in place, according to the invention.
FIG. 19 is a schematic perspective view of the insertion tool of FIG. 18 with a second electrode in place.
Figure 20:
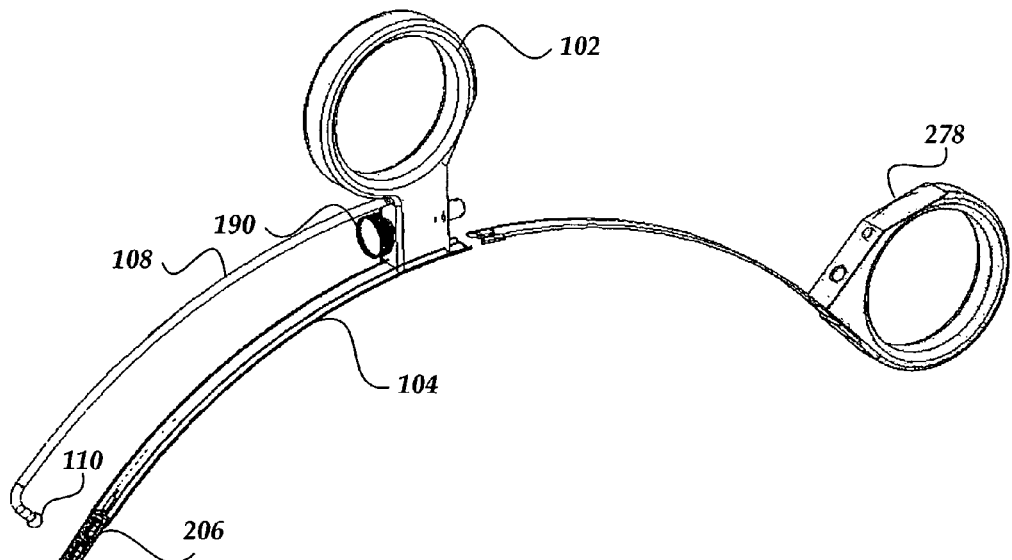
FIG. 20 is a schematic perspective view of the insertion tool of FIG. 19 with the inserter removed.

FIGS. 18-20 illustrate another embodiment of an insertion tool and a method for its use. This embodiment is similar to that illustrated in FIGS. 15-17 with the insertion member 104 having a portion that is inserted into the patient and which has the form of a hollow tube with openings (not shown) at each end. The electrode 106 is carried on an inserter 178 that can be inserted through opening 174 and the electrode 106 can be pushed along the hollow tube until the electrode 106 is pushed out of opening, as illustrated in FIG. 18. The electrode 106 is coupled to the electrode control device 170 (FIG. 1) typically through the inserter member 104 using a cord or leads or the like.

The configuration of the handle 102 allows the practitioner to manipulate the insertion tool to identify the target tissue. The handle 102 illustrated in FIGS. 18-20 is a ring in which the practitioner can insert a finger (or, optionally, more than one finger.) The inserter 178 can also include a ring in which the practitioner can insert one or more fingers. This provides the practitioner with a useful configuration for guiding the inserter 178 into the insertion member 104. The alignment member 108 of this embodiment extends from the handle 102 and terminates in a marker 110 or pointer. In one embodiment, the marker 110 can include ink or other media disposed on the marker for marking the skin when the desired implantation site is found. The insertion member 104 can be flexed to move the marker 110 into contact with the skin of the patient. In yet other embodiments, a pointer is used instead of a marker 110.

The insertion tool 100 can also include an optional fastening device 190 to fasten the inserter 178 to the handle 102. This can stabilize the insertion tool during the tissue identification procedure. The fastening device 109 can be, for example, a screw, clamp, bolt/nut, or any other arrangement that can temporarily hold the inserter and handle together. As one alternative, the fastening device can be attached to the inserter 178 instead of the handle 102.

Once the desired electrode position for stimulation has been determined using electrode 106 to find the tissue to be stimulated, the electrode 106 and inserter 178 can be removed from the insertion member 104 without removing the insertion member from the patient. A microstimulator electrode 206 can then be inserted into the opening in the insertion member and pushed through the hollow tube of the insertion member 104 using a second inserter 278 while the insertion member 104 is still in the patient (if desired), as illustrated in FIGS. 19 and 20. This second inserter 278 may be simply a device that pushes on the electrode 206 or the second inserter may include an electrode holder similar to the electrode holder 230 of FIG. 5, as illustrated in FIG. 20. Again, the inserter 278 can include a ring for guiding the inserter into the insertion member 104. Also, if desired, the fastening member 190 can be used to hold the handle 102 and insertion member 278 together. This may be useful if the insertion tool will be repositioned due to movement during the process of removing insert 178 and inserting electrode 206 using inserter 278 or if further movement is desired to identify the target tissue using the electrode 206. After positioning the electrode 206, the insertion member 104 can be removed through the incision in the patient leaving the electrode. In all embodiments, the inserters 178 and 278 can be considered a removable portion of the insertion member 104.

Figure 11:
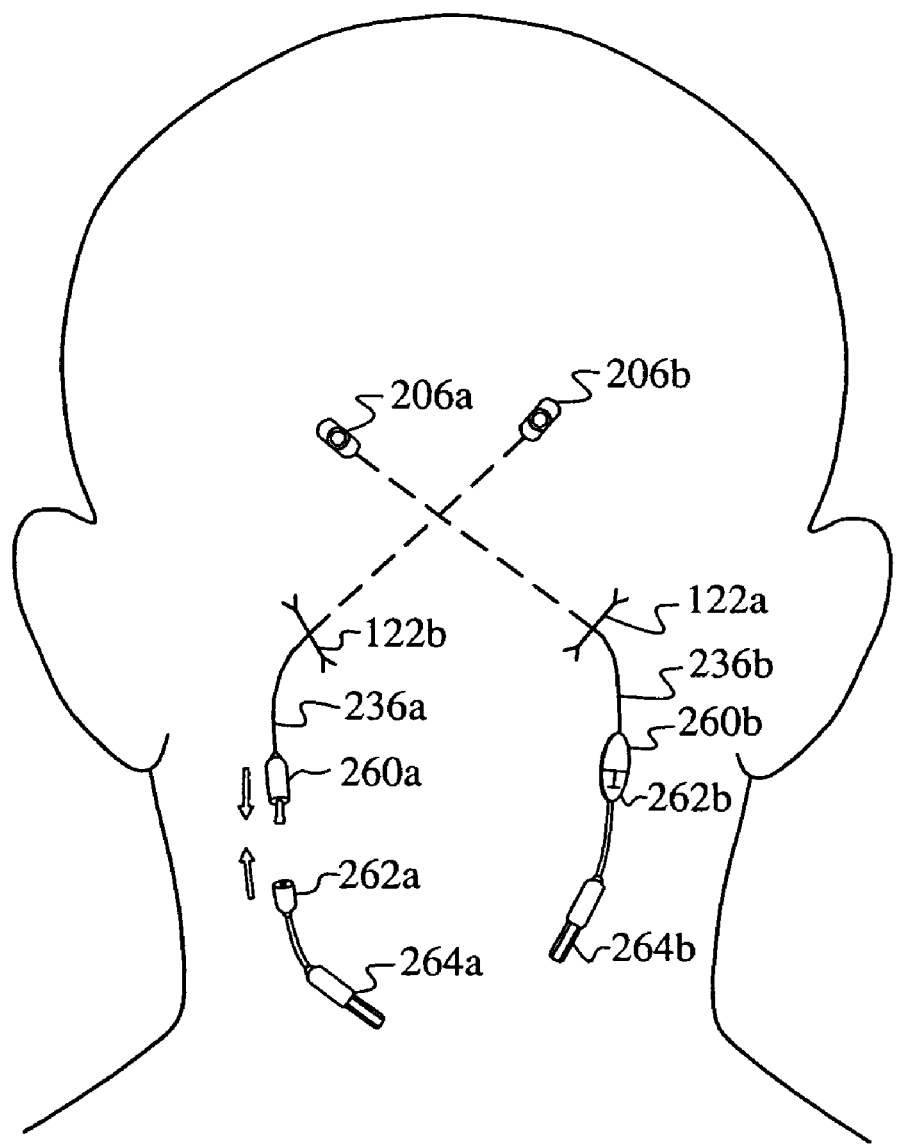
FIG. 11 is a schematic view of two electrodes implanted near the occipital nerve of a patient, according to the invention.

FIG. 11 illustrates two electrodes 206, 206' that have each been implanted individually through incisions 122, 122', respectively, using the insertion tool(s) described above. It will be understood that other embodiments include the implantation of a single electrode or three or more electrodes. It will also be understood that, although the Figures illustrate implantation of electrodes to stimulate the occipital nerve, electrodes can also be implanted to stimulate other nerves or tissues using the insertion tool(s).

Figure 12:
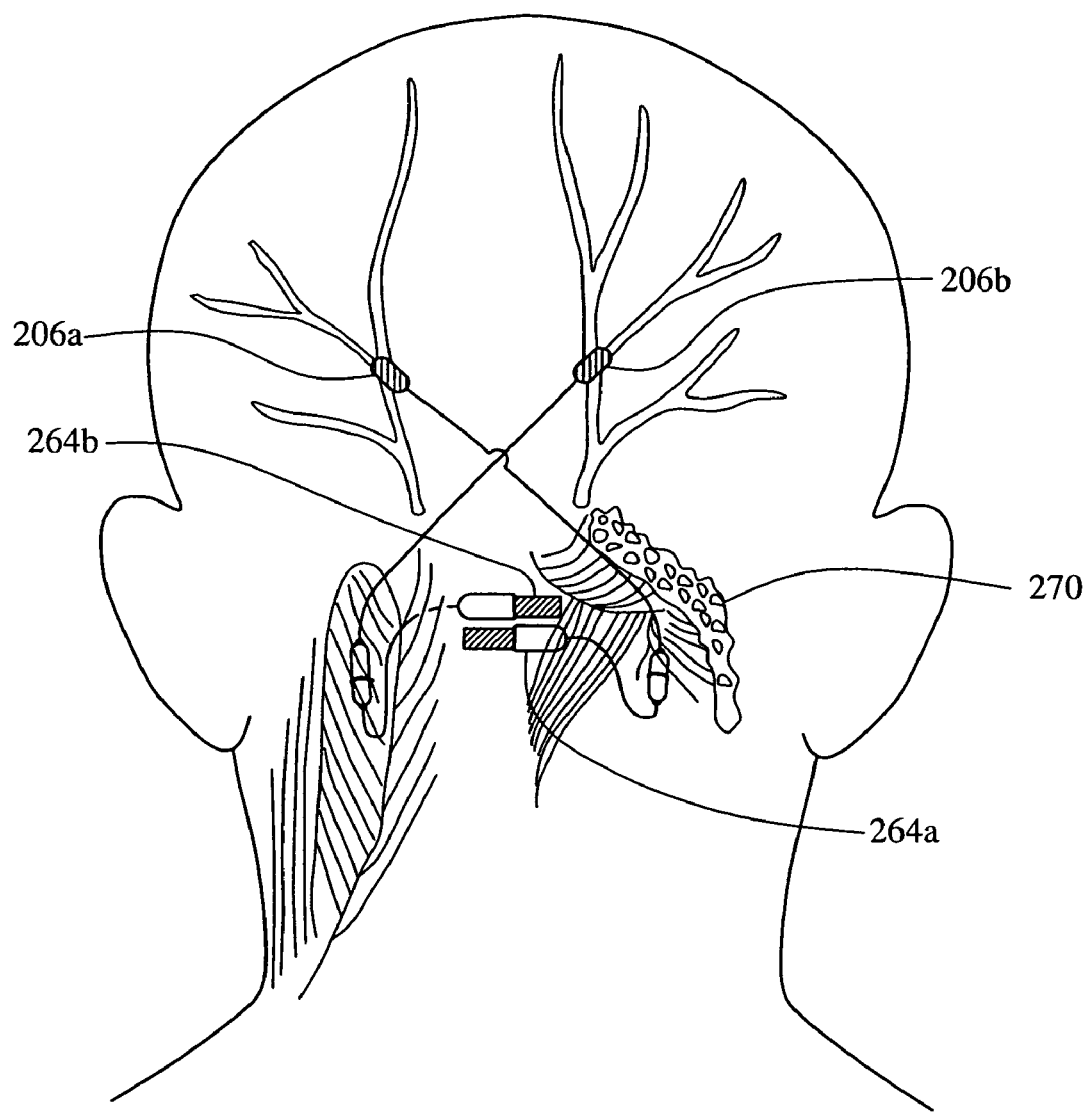
FIG. 12 is a schematic view of the implantation of two microstimulators coupled to the electrodes illustrated in FIG. 11, according to the invention.

Once implanted, a connector 260, 260' attached to the lead 236, 236' is coupled to a connector 262, 262' attached to a microstimulator unit 264, 264'. The microstimulator unit(s) 264, 264' can then be implanted under the skin, for example, under the trapezius muscles 270 at the base of the skull, as illustrated in FIG. 12. Preferably, the microstimulator unit can be implanted using the same incision used to implant the electrode. The incision can then be closed. The microstimulator unit provides stimulation signals to the microstimulator electrode to stimulate the occipital nerve (or other nerves or tissues) to treat a disorder or disease, such as headaches and migraines.

Figure 13:
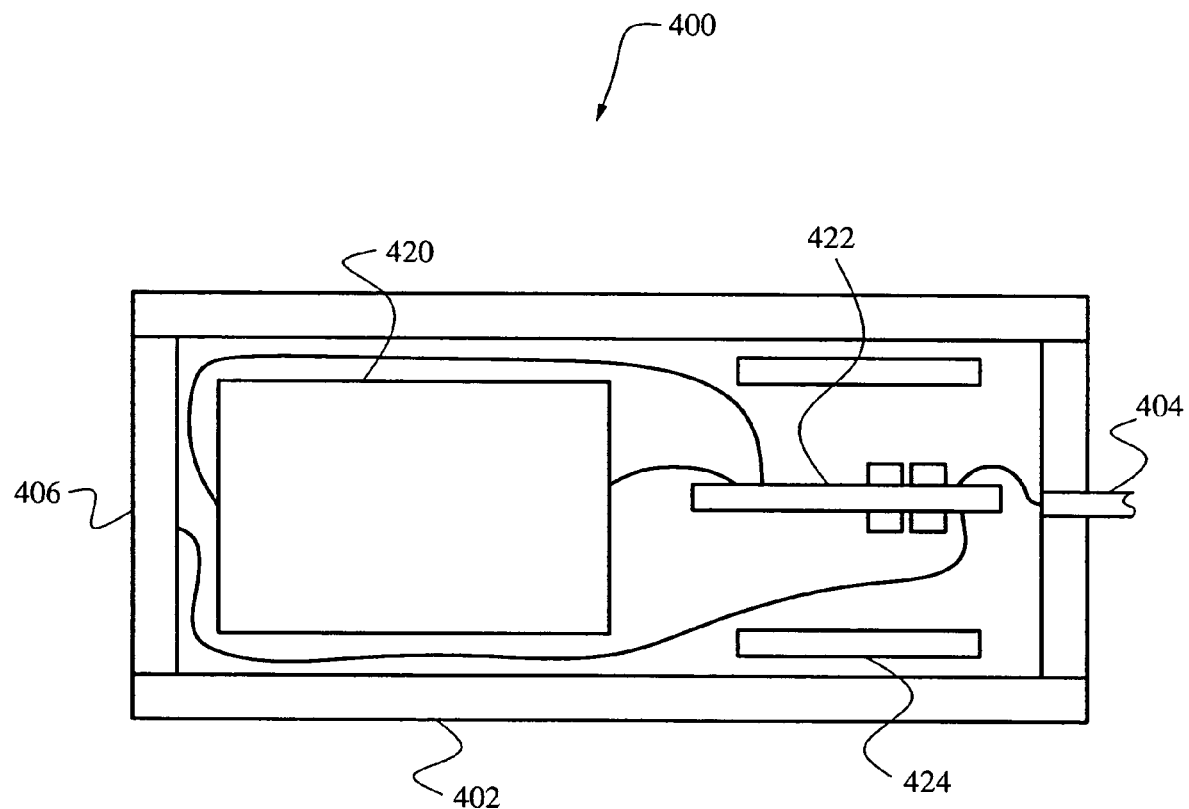
FIG. 13 is a schematic cross-sectional view of one embodiment of a microstimulator unit, according to the invention.

FIG. 13 illustrates one embodiment of an implantable microstimulator unit 400. The implantable microstimulator unit 400 includes a housing 402, a lead 404 that couples the microstimulator to the electrode 206 via the lead 236 (see FIG. 11), a second electrode 406, a power source 420, an electronics subassembly 422, and an optional antenna 424. Other embodiments of an implantable microstimulator may include more or fewer components. It will be understood that the power source 420 and/or components of the electronics subassembly 422 and/or the optional antenna 424 can be provided outside of the housing in a separate unit and coupled to the implantable microstimulator by a lead. The implantable microstimulator unit can be implanted in any suitable area of the patient.

The housing 402 can be formed of one or more pieces and using any material including, but not limited to, metals, alloys, ceramics, and plastics. Preferably, the housing resists the transport of moisture into the interior of the housing and is sufficiently sturdy to protect the components on the interior of the housing from damage under expected implantation and usage conditions.

The housing can have any shape including, for example, cylindrical, conical, parallelepiped, cubic, and the like. In at least some embodiments, a cylindrical shape is preferred. The lateral cross-sectional dimensions can be the same or can vary along the length of the housing. In one embodiment, the housing has a cylindrical shape with a uniform diameter along the length of the housing. The uniform diameter can be, for example, no greater then 5 mm, no greater than 4 mm, no greater than 3.3 mm, or no greater than 3 mm. This uniform diameter can be in the range of from, for example, 1 to 5 mm. In another embodiment, the housing is a cylinder that is wider at the ends and narrower in the middle or the housing is a cylinder that is wider in the middle and narrower at the ends.

In at least some embodiments, the length of the implanted microstimulator unit is no greater than 30 mm. For example, the length of the implanted microstimulator unit can be in the range of 10 to 30 mm.

The electrodes 206 (see FIG. 11), 406 typically form the anode and cathode of the microstimulator. These electrodes can be formed of the same or different conductive materials. Preferably, the electrodes are formed of materials that do not substantially corrode under the operating conditions and in the operating environment for the expected lifetime of the microstimulator. Examples of suitable materials include metals, alloys and other conductive materials such as, for example, titanium, iridium, platinum, platinum iridium, stainless steel, and the like. In an alternative embodiment, both electrodes may be implanted near the nerve or other tissue to be stimulated with leads from the microstimulator provided to both electrodes.

The electrode 406 can be an electrode attached to the housing of the microstimulator unit (e.g., disposed at an end of the microstimulator unit), as illustrated in FIG. 13. Alternatively, the electrode 406 can be implanted elsewhere (e.g., near the tissue to be stimulated) and coupled to the microstimulator unit via a lead.

A power source 420 can be disposed within the housing 400. Any power source can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 424 or a secondary antenna. The external power source can be in a device that is mounted on the skin of the user or in a unit that is provided near the microstimulator user on a permanent or periodic basis.

If the power source 420 is a rechargeable battery, the battery may be recharged using the optional antenna 424, if desired. Power can be provided to the battery 420 for recharging by inductively coupling the battery through the antenna to a recharging unit 510 (see FIG. 14) external to the user. Examples of such arrangements can be found in the microstimulator references identified above.

Figure 14:
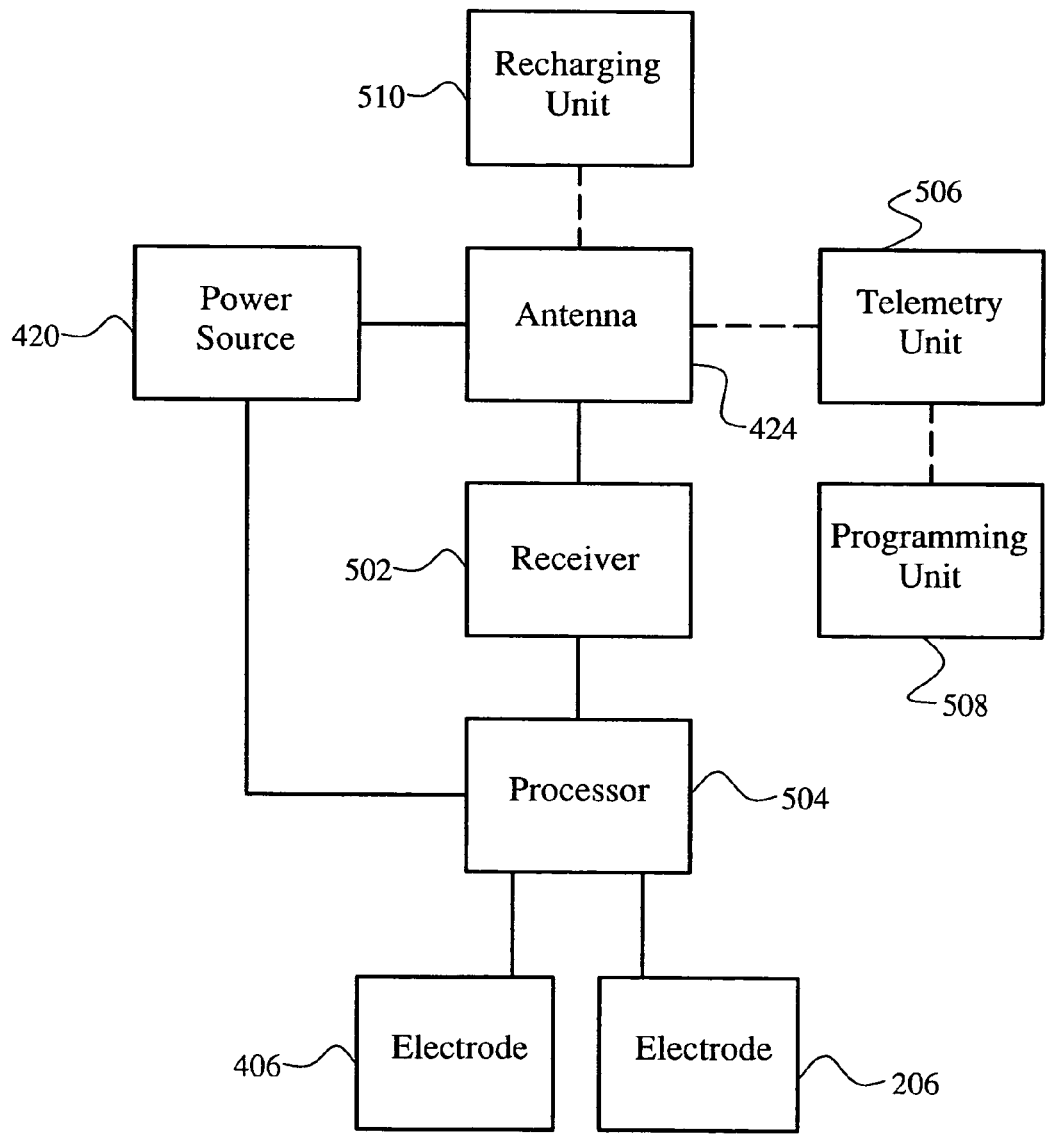
FIG. 14 is a schematic overview of components for a system for microstimulation of body tissues, according to the invention.

In one embodiment, electrical current is emitted by the electrodes to simulate the nerve. The electronic subassembly 422 provides the electronics used to operate the microstimulator and generate the electrical pulses at the electrodes to produce stimulation of the nerve. FIG. 14 illustrates one embodiment of components of the electronic subassembly and associated units. It will be understood that the electronic subassembly can include more, fewer, or different components and can have a variety of different configurations including those configurations disclosed in the microstimulator references cited above. Some or all of the components of the electronic subassembly can be positioned on one or more circuit boards or similar carriers within the housing, if desired.

In the illustrated embodiment, a processor 504 is provided to control the timing and electrical characteristics of the microstimulator. For example, the processor can, if desired, control one or more of the timing, frequency, strength, duration, and waveform of the pulses. Any processor can be used and can be as simple as an electronic device that produces pulses at a regular interval or the processor can be capable of receiving and interpreting instructions from an external programming unit 508 that allow modification of pulse characteristics. In the illustrated embodiment, the processor 504 is coupled to a receiver 502 which, in turn, is coupled to the optional antenna 424. This allows the processor to receive instructions from an external source to direct the pulse characteristics.

In one embodiment, the antenna 424 is capable of receiving signals (e.g., RF signals) from an external telemetry unit 506 which is programmed by a programming unit 508. The programming unit 208 can be external to, or part of, the telemetry unit 506. The telemetry unit 506 can be a device that is worn on the skin of the user or can be carried by the user and can have a form similar to a pager or cellular phone, if desired. As another alternative, the telemetry unit may not be worn or carried by the user but may only be available at a home station or at a practitioner's office. The programming unit 508 can be any unit that can provide information to the telemetry unit for transmission to the implanted microstimulator. The programming unit 508 can be part of the telemetry unit 506 or can provide signals or information to the telemetry unit via a wireless or wired connection. One example of a suitable programming unit is a computer operated by the user or practitioner to send signals to the telemetry unit.

The signals sent to the processor 504 via the antenna 424 and receiver 502 can be used to modify or otherwise direct the operation of the microstimulator. For example, the signals may be used to modify the pulses of the microstimulator such as modifying one or more of pulse duration, pulse frequency, pulse waveform, and pulse strength. The signals may also direct the microstimulator to cease operation or to start operation or to start charging the battery.

Optionally, the microstimulator can include a transmitter (not shown) coupled to the processor and antenna for transmitting signals back to the telemetry unit 506 or another unit capable of receiving the signals. For example, the microstimulator may transmit signals indicating whether the microstimulator is operating properly or not or indicating when the battery needs to be charged. The processor may also be capable of transmitting information about the pulse characteristics so that a user or clinician can determine or verify the characteristics.

The optional antenna 424 can have any form. In one embodiment, the antenna comprises a coiled wire that is wrapped at least partially around the electronic subassembly within the housing.

The insertion tools 100, 200 with electrode 106 and, optionally, electrode 206 can be provided as a kit or as separate components. For example, a kit can include a handle 102, 202 with an attached alignment member 108, 208, a first insertion member 104 with electrode 106, and a second insertion member 204. The kit can optionally include one or more of the following: a marker 110, a pointer 214, and a second electrode 206.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An insertion kit for implanting an electrode in a patient, comprising:

a handle;

an insertion member coupleable to the handle at a proximal end of the insertion member and configured and arranged to be inserted into a patient;

an alignment member coupled to the handle and configured and arranged to be disposed over a distal end of the first insertion member when the first insertion member is coupled to the handle;

an electrode configured and arranged to be inserted into the patient using the insertion member; and a marker, wherein the marker and the alignment member are configured and arranged for coupling the marker to the alignment member for making a mark on the skin of the patient to mark a position of the electrode, wherein the marker, alignment member, handle, insertion member, and electrode are configured and arranged so that the marker is positioned over the electrode when the marker is coupled to the alignment member, the electrode is coupled to the insertion member, and the insertion member is coupled to the handle.

2. The insertion kit of claim 1, wherein the insertion kit further comprises a pointer that is detachably coupleable to the alignment member to find the marked position on the skin of the patient for placement of the electrode at the marked position.

3. The insertion kit of claim 1, wherein the insertion member is detachably coupled to the handle.

4. The insertion kit of claim 1, further comprising a second electrode and a second insertion member configured and arranged for detachably coupling to the handle in place of the insertion member, wherein the first electrode is permanently coupled to the first insertion member and the second electrode is detachably coupleable to the second insertion member.

5. The insertion kit of claim 1, wherein the insertion member comprises an electrode holder disposed at a distal end of the insertion member and the electrode is disposed in the electrode holder of the insertion member.

6. The insertion kit of claim 5, wherein the electrode is detachably coupleable to the electrode holder.

7. The insertion kit of claim 5, wherein the electrode holder comprises two pairs of opposing rails, wherein each pair of opposing rails is configured and arranged to receive and hold an edge portion of the electrode between the opposing rails of the pair.

8. The insertion kit of claim 7, wherein the electrode comprises a raised rim along the edge portion of the electrode.

9. The insertion kit of claim 5, further comprising a plurality of protrusions disposed on at least one surface of the electrode and configured and arranged to assist in detaching the electrode from the electrode holder to implant the electrode in a body of a patient, wherein each protrusion is smaller than the electrode.

10. The insertion kit of claim 5, wherein the electrode holder comprises two pairs of opposing rails configured and arranged to hold the electrode between the opposing rails, wherein each pair of opposing rails has a U-shaped form and an edge portion of the electrode fits inside the pair of opposing rails to hold the electrode between the pair of opposing rails.

11. The insertion kit of claim 5, further comprising a plurality of protrusions disposed on at least one surface of the electrode and configured and arranged to assist in detaching the electrode from the electrode holder to implant the electrode in a body of a patient, wherein each protrusion has a smaller surface area than the electrode.

12. The insertion kit of claim 5, further comprising a plurality of conical protrusions disposed on at least one surface of the electrode and configured and arranged to assist in detaching the electrode from the electrode holder to implant the electrode in a body of a patient.

13. The insertion kit of claim 1, wherein the marker is configured and arranged for making the mark in ink on the skin of the patient.

14. The insertion kit of claim 1, wherein the marker is detachably coupleable to the alignment member.

15. The insertion kit of claim 1, wherein the alignment member defines an opening for receiving the marker in the alignment member.

16. The insertion kit of claim 15, further comprising a pointer configured and arranged to be received in the opening of the alignment member.

17. The insertion kit of claim 1, wherein the electrode is configured and arranged for implantation beneath the scalp of a patient.

18. The insertion kit of claim 1, further comprising a microstimulator, the microstimulator comprising a housing, and a power source and an electronic subassembly disposed within the housing and configured and arranged to provide stimulation pulses to the electrode, the electrode being disposed on or as part of the housing.

19. The insertion kit of claim 18, wherein the microstimulator has a length that is no greater than 30 mm.

20. The insertion kit of claim 1, wherein a portion of the insertion member is curved to roughly follow a curvature of a scalp of a patient.

* * * * *